(12) United States Patent
Opsal (10) Patent No.: US 7,436,527 B2
(45) Date of Patent: *Oct. 14, 2008

(54) SYSTEMS AND METHODS FOR IMMERSION METROLOGY

(75) Inventor: Jon Opsal, Livermore, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/732,125

(22) Filed: Apr. 2, 2007

(65) Prior Publication Data

US 2008/0024780 A1 Jan. 31, 2008

Related U.S. Application Data

(63) Continuation of application No. 10/794,094, filed on Mar. 4, 2004, now Pat. No. 7,215,431.

(51) Int. Cl.
*G01B 11/28* (2006.01)
*G01B 11/06* (2006.01)

(52) U.S. Cl. .................. 356/630; 356/635; 356/124

(58) Field of Classification Search .................. 356/630, 356/632, 635, 124; 250/559.19, 559.24, 250/559.27, 559.28
See application file for complete search history.

(56) References Cited

U.S. PATENT DOCUMENTS

| 4,999,014 | A | | 3/1991 | Gold et al. | ............... 356/382 |
| 5,042,951 | A | | 8/1991 | Gold et al. | ............... 356/369 |
| 5,121,256 | A | | 6/1992 | Corle et al. | ............... 359/664 |
| 5,181,080 | A | * | 1/1993 | Fanton et al. | ............... 356/632 |
| 5,412,473 | A | | 5/1995 | Rosencwaig et al. | ......... 356/351 |
| 5,596,411 | A | | 1/1997 | Fanton et al. | ............... 356/369 |
| 5,610,683 | A | | 3/1997 | Takahashi | ............... 355/53 |
| 5,798,837 | A | * | 8/1998 | Aspnes et al. | ............... 356/369 |
| 5,877,859 | A | | 3/1999 | Aspnes et al. | ............... 356/364 |
| 5,900,354 | A | | 5/1999 | Batchelder | ............... 430/395 |
| 5,953,446 | A | | 9/1999 | Opsal et al. | ............... 382/141 |
| 6,411,434 | B1 | | 6/2002 | Eastman et al. | ............ 359/398 |
| 6,429,943 | B1 | | 8/2002 | Opsal et al. | ............... 356/625 |

(Continued)

FOREIGN PATENT DOCUMENTS

WO  WO 99/02970  1/1999

OTHER PUBLICATIONS

J.M. Leng et al., "Simultaneous measurement of six layers in a silicon on insulator film stack using spectrophotometry and beam profile reflectometry," *J. Appl. Phys.*, vol. 81, No. 8, Apr. 15, 1997, pp. 3570-3578.

(Continued)

*Primary Examiner*—Roy M Punnoose
(74) *Attorney, Agent, or Firm*—Stallman & Pollock LLP (57) ABSTRACT

Fluid immersion technology can be utilized to increase the resolution and angular range of existing metrology systems. An immersion fluid placed between the metrology optics and the sample can reduce the refraction at the sample interface, thereby decreasing the spot size of the beam on a feature of the sample while simultaneously increasing the angular range of the system. The decreased spot size, in combination with an increased angular spread, allows an existing metrology system to measure parameters of a sample, such as a semiconductor or microelectronic device, with improved resolution and without expensive and/or complex changes to the mechanics of the metrology system.

18 Claims, 3 Drawing Sheets

U.S. PATENT DOCUMENTS

| | | | | |
|---|---|---|---|---|
| 6,813,034 | B2 | 11/2004 | Rosencwaig et al. | 356/601 |
| 6,891,596 | B2 | 5/2005 | Rostalski et al. | 355/53 |
| 6,934,024 | B2 | 8/2005 | Zhan et al. | 356/369 |
| 2004/0240047 | A1 | 12/2004 | Shafer et al. | 359/366 |
| 2004/0263959 | A1* | 12/2004 | Dixon et al. | 359/385 |

OTHER PUBLICATIONS

B.W. Smith, "Immersion Optical Lithography at 193nm," *Future Fab Intl.*, vol. 15, Jul. 11, 2003, 11 pages in length.

H. Hogan, "New Semiconductor Lithography Makes a Splash," *Photonics TechnologyWorld* (http://photonics.com/spectra/tech/XQ/ASP/techid.1589/placement.HomeIndex/QXR/r...) Oct. 2003 Edition, 3 pages in length.

"Technology backgrounder: Immersion Lithography," copyright 2003 IC Knowledge, from ICKnowledge.com, pp. 1-5.

D. Lammers, "Scanners take the plunge,"0 *EETimes* (http://eet.com/issue/fp/OEG20040202S0014), Feb. 2, 2004, 5 pages in length.

D. Lammers, "Immersion could extend to 22-nm node," *EETimes* (http://www.eetimes.com/printableArticle?doc_id=OEG20040127S0023), Jan. 27, 2004, 2 pages in length.

J.T. Fanton et al., "Multiparameter measurements of thin films using beam-profile reflectometry," *J. Appl. Phys.*, vol. 73, No. 11, Jun. 1, 1993, pp. 7035-7040.

X. Niu et al., "Specular Spectroscopic Scatterometry in DUV Lithography," *SPIE* (part of the SPIE Conference on Metrology, Inspection, and Process Control of Microlithography XIII, Santa Clara, California), vol. 3677, Mar. 1999, pp. 159-168.

N. Jakatdar et al., "In-situ Metrology for Deep Ultraviolet Lithography Process Control," *SPIE*, vol. 3332 (1998), pp. 262-270.

* cited by examiner

SYSTEMS AND METHODS FOR IMMERSION METROLOGY

CLAIM OF PRIORITY

This application is a continuation of U.S. patent application Ser. No. 10/794,094, filed Mar. 4, 2004, now U.S. Pat. No. 7,215,431 entitled "SYSTEMS AND METHODS FOR IMMERSION METROLOGY" which is and incorporated herein by reference.

TECHNICAL FIELD OF THE INVENTION

The present invention relates to the examination of features on semiconductors and microelectronic devices.

BACKGROUND

As the dimensions of microelectronic devices continue to shrink, and device density continues to increase, the metrology requirements for process development, monitoring, and control continue to tighten accordingly. The accuracy of parameter measurements is becoming increasingly important to optimizing both device performance and chip yield. In order to obtain an accurate and robust monitoring solution, and to avoid being surpassed by advances in microelectronics fabrication, the measurement sensitivity of metrology tools must continue to improve.

For example, the need for accurately measuring the thickness and/or composition of thin films is particularly acute in the semiconductor manufacturing industry where the thickness of these thin film oxide layers on semiconductor substrates is measured. To be useful, the measurement system must be able to determine the thickness and/or composition of films with a high degree of accuracy. There also is a need to increase the resolution of metrology systems to accurately measure dimensions of features such as so-called critical dimension ("CD"), which typically refers to the minimum line width that can be fabricated for a microelectronic device. Presently, the CD of a single line feature is on the order of about 90 nm, which is difficult to measure optically. As the critical dimensions push towards the 45 nm range, there is a need for improved measurement techniques and a desire to minimize the additional cost necessary to develop such techniques.

Presently preferred measurement systems rely on non-contact, optical measurement techniques, which can be performed during a semiconductor manufacturing process without damaging the wafer sample. Such optical measurement techniques include directing a probe beam to the sample over a relatively large area and measuring one or more optical parameters of the reflected probe beam. Such a large-scale approach can be inadequate for increasingly small features, as the shape and size of such sub-micron features can be difficult to measure with such an approach.

In order to increase measurement accuracy and to gain additional information about the target sample, a number of optical measuring devices can be incorporated into a single composite optical measurement system. For example, the present assignee has marketed a product called OPTI-PROBE, which incorporates many systems, including a Beam Profile Reflectometer (BPR), a Beam Profile Ellipsometer (BPE), and a Broadband Reflective Spectrometer (BRS). Each of these devices can measure parameters of optical beams reflected by, or transmitted through, a target sample. Detailed descriptions of assignee's multiple angle of incidence devices can be found in the following U.S. Pat. Nos. 4,999,014; 5,042,951; 5,181,080; 5,412,473; 5,596,411; and 6,429,943, all of which are hereby incorporated herein by reference. The composite measurement system can combine the measured results of each of the measurement devices to precisely derive the thickness and composition of a thin film and substrate of a target sample, and/or to measure critical dimensions and feature profiles of periodic structures on samples such as semiconductor wafers. A summary of metrology devices currently found in the Opti-Probe can be found in PCT application WO/9902970, published Jan. 21, 1999. The precision of the results measured by such a system, however, still can be limited by the resolution of each of the combined systems.

BRIEF DESCRIPTION OF THE DRAWINGS

FIG. 2 is a diagram of a sample interface at (a) air and at (b) an immersion fluid.

DETAILED DESCRIPTION

Figure 1:
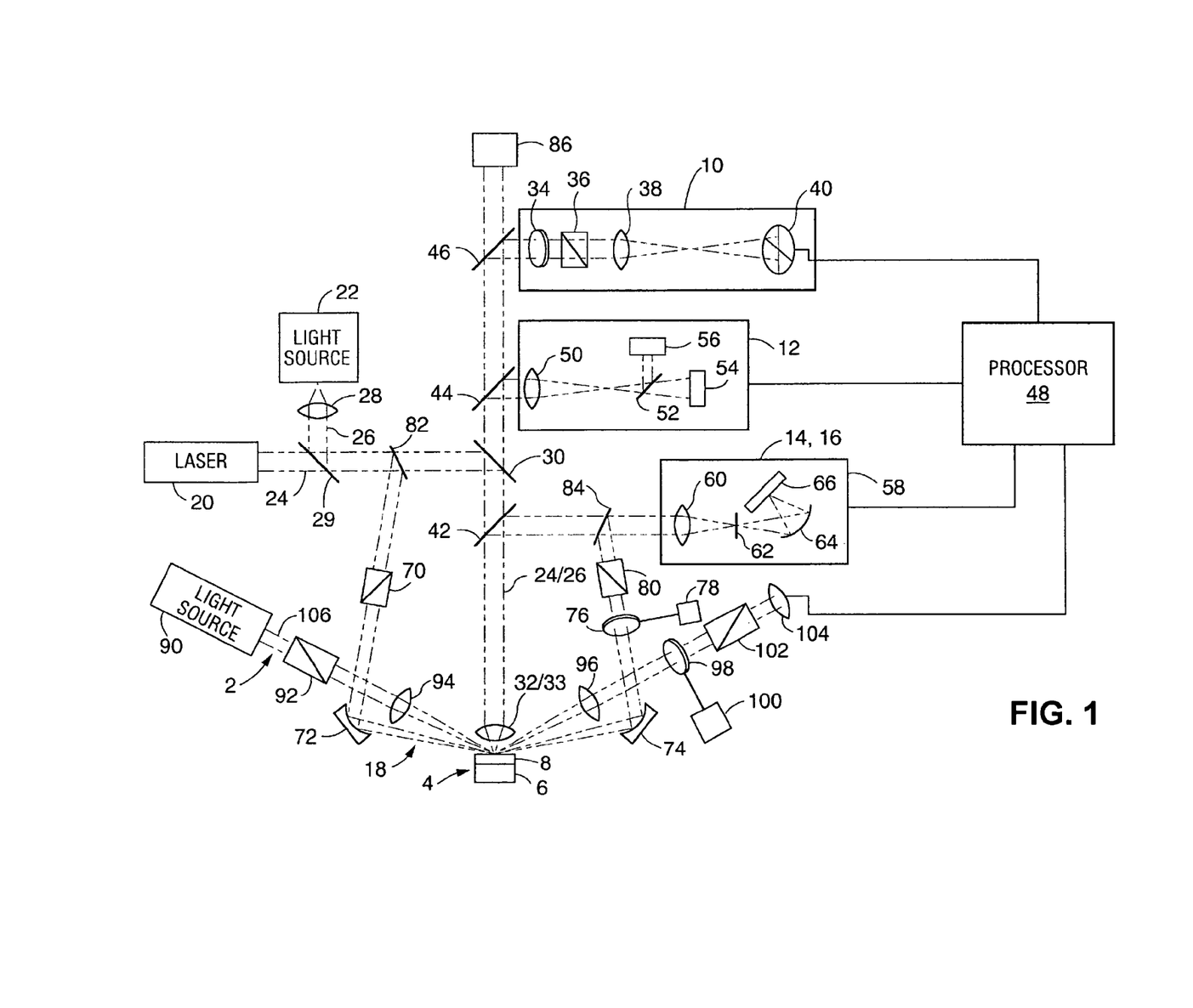
FIG. 1 is a diagram of a metrology system that can be used in accordance with various embodiments of the present invention.

FIG. 1 illustrates a composite optical measurement system 1 that has been developed by the present assignees, which includes a number of different non-contact optical measurement devices. Composite optical measurement system 1 includes a Beam Profile Ellipsometer (BPE) 10, a Beam Profile Reflectometer (BPR) 12, a Broadband Reflective Spectrometer (BRS) 14, a Deep Ultra Violet Reflective Spectrometer (DUV) 16, a Broadband Spectroscopic Ellipsometer (BSE) 18, and a narrowband ellipsometer 2. This particular combination of optical measurement devices can utilize two optical sources, which in this example include laser 20 and white light source 22. Laser 20 can generate probe beam 24, and white light source 22 can generate probe beam 26, which is collimated by lens 28 and directed along the same path as probe beam 24 by mirror 29. Laser 20 can be any appropriate laser, such as a solid state laser diode from Toshiba Corp. which emits a linearly polarized 3 mW beam at 673 nm. White light source 22 can be any appropriate light source, such as a deuterium-tungsten lamp that produces a 200 mW polychromatic beam that covers a spectrum of 200 nm to 800 nm. The probe beams 24, 26 are reflected by mirror 30 and pass through mirror 42 to the sample 4.

The probe beams 24, 26 are focused onto the surface of the sample with a lens 32. In one embodiment, two lenses 32, 33 are mounted in a turret (not shown) and are alternatively movable into the path of probe beams 24 and 26. Lens 32 is a spherical, microscope objective lens with a high numerical aperture (on the order of 0.90 NA) to create a relatively large spread of angles of incidence with respect to the sample surface, and to create a spot size of about one micron or less in diameter. Lens 33 can have a relatively lower numerical aperture (on the order of 0.4 NA) and can be capable of focusing deep UV light to a spot size of about 10-15 microns. As discussed above, such spot sizes can be problematic for measuring structures such as those having a critical dimension on the order of 90 nm or less.

Immersion Metrology

Systems and methods in accordance with embodiments of the present invention can increase the resolution of existing metrology systems, such as the system shown in FIG. 1, and increase the amount of angular spectral information obtained for processes such as BPE and BPR by utilizing any of a number of fluid immersion techniques. Fluid immersion can allow a metrology system such as a reflectometer or ellipsometer device to determine various characteristics of microstructures and thin films with improved precision. Such characteristics can include material composition, thickness, index of refraction, absorption, stress, critical dimension, profile dimension, and surface roughness. Fluids used for such immersion approaches can be any appropriate liquid or fluid having an appropriate index of refraction and sufficient transparency to the working light wavelength. For example, immersion fluids based on perfluoropolyethers (PFPE) are sufficiently transparent for 157 nm wavelengths, and are compatible with many photoresist and other materials used in microelectronic fabrication. One such immersion fluid has a refractive index $n_i$=1.37 at a wavelength of 157 nm. Other immersion fluids can include purified water, which can have an index of refraction of about 1.43, or other ionized or "doped" liquids, such as mixtures of purified water with any of a number of phosphates, sulfates, and alkalines capable of producing a liquid with an index of refraction higher than that of purified water alone.

When using liquid immersion technology with reflectometry or ellipsometry, for example, light from a light source can be directed through an immersion liquid, as described elsewhere herein. The liquid will have a surface area that is either directly in contact with, or adjacent to, the film or structure being examined. The incident light, which can be polarized (e.g., linearly, circularly, or elliptically), can be directed into the immersion liquid such that the radiation can be reflected off the surface and/or a layer of the sample and can be directed to an analyzer or detector for examination. Characteristics of the sample/layer then can be determined, such as by comparing the measurements with a theoretical model based on the possible values of those characteristics. The model can provide a relationship between the characteristics of the sample and the measurable parameters. Fitting algorithms can be used, iteratively where necessary, to determine the characteristics of the sample using the measured parameters and theoretical model.

Figure 2A:
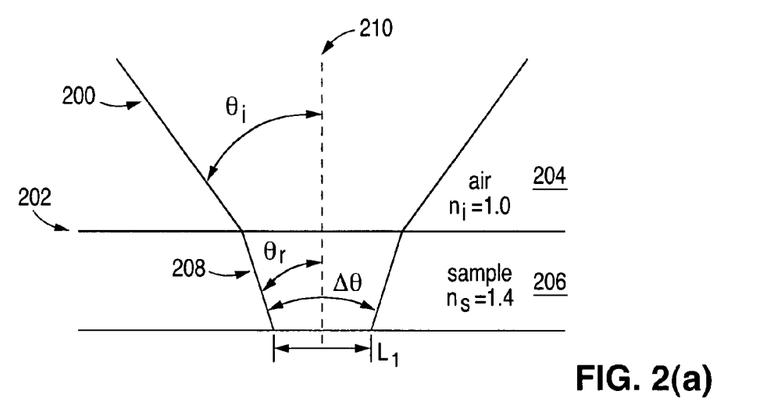
Figure 2B:
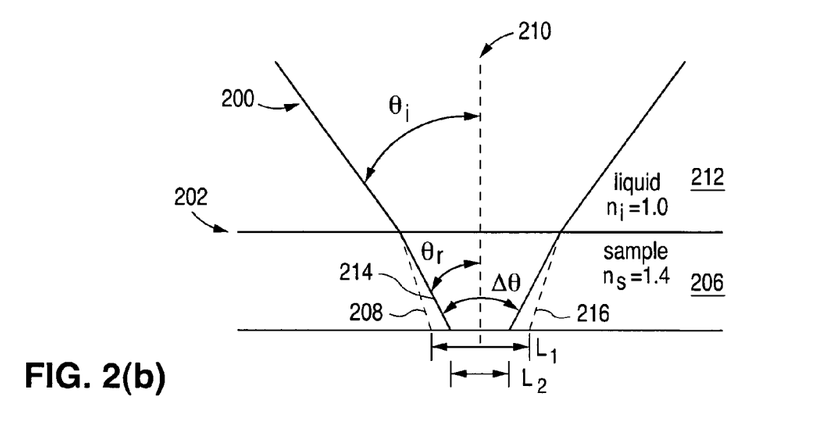

Advantages of fluid immersion metrology can be discussed with respect to the basic physical law of refraction, commonly known as Snell's Law, and with respect to FIGS. 2(a) and 2(b). FIGS. 2(a) and 2(b) are exaggerated for purposes of explanation and are not intended to be to scale. When a beam of incident light 200, for example, encounters an interface 202 between two media, such as air 204 and a sample layer 206, the beam will pass through the sample layer 206 as a transmitted beam 208 that is refracted within the same plane of incidence (the plane of the Figure). A portion of the beam (not shown) also can be reflected from the interface at an angle of reflection as known in the art. The angle at which the transmitted beam passes through the sample layer 206 relative to a normal 210 to the interface is commonly referred to as the angle of refraction, $\theta_r$, and is dependent upon the index of refraction of the sample layer, $n_s$. The angle of refraction is related to the angle of incidence $\theta_i$ and the refractive index of the incident medium, $n_s$, by Snell's Law, given by:

$$n_i * \sin \theta_i = n_s * \sin \theta_r.$$

If the refractive index of each of the two media is the same, such as both at 1.4, there will be substantially no refraction as the beam passes through the layer. Where the two media have differing indices of refraction, such as for air and a sample as in FIG. 2(a), the beam will refract to form a spot of diameter $L_1$ at a layer, surface, or interface of the sample.

FIG. 2(b) shows the same setup as FIG. 2(a), except that the first media (air in FIG. 2(a)) has been replaced with an immersion fluid 212 of refractive index 1.2. Using Snell's law given above, it can be seen that increasing the refractive index of the first medium results in less refraction of the light beam in the second medium 206. The resulting refracted beam 214 will create a spot at the bottom of the sample layer 206 of diameter $L_2$, which is smaller than the spot of diameter $L_1$ created by beam portion 208 from the air example of FIG. 2(a). Further, utilizing a first medium having a higher index of refraction can increase the total angular range of the light focused on the sample. For instance, for an angle of incidence of 20° for each of the exterior rays of the beam as shown in FIG. 2(b), and using air ($n_i$=1.0) as the first media, the refractive angular range $\Delta\theta$ of the beam is given by:

$$\Delta\theta = 2\theta_i = 2*\sin^{-1}\left(\frac{1}{1.4}*\sin(20°)\right) = 2*(14.14°) = 28.28°$$

Then, for the second example wherein an immersion fluid of water ($n_i$=1.2) is used as the first media, the refractive angular range of the beam is given by:

$$\Delta\theta = 2\theta_i = 2*\sin^{-1}\left(\frac{1.2}{1.4}*\sin(20°)\right) = 2*(17.047°) = 34.09°$$

In addition to decreasing the size of the spot on a layer or feature of the sample such that a lateral resolution of the system is increased, an increase in the angular range results in an increase in the number of angles which can be measured by the focused probe beam, thereby increasing the amount of angular spectral information that can be obtained by the metrology system for a given initial beam size and optical configuration. This can be of significance for many measurement systems, including and in addition to those described herein such as BPR and BPE, as different information can be obtained for each angle at which the sample is examined. Each additional angle can function as a separate independent measurement of the sample, as each additional ray hits the sample with a different incident angle and with a different path length. Thus, additional reflectivity information can be obtained. Further, measurement sensitivity can be increased by increasing the angular range of the system. For example, in ellipsometry the information obtained at higher angles, such as angles around Brewster's angle as known in the art, can be most sensitive to subtle variations in the sample. Using fluid immersion with a normal incidence BPE system, for example, allows for a small spot to be focused on the sample at normal incidence but with a large angular range.

Such improvements can be beneficial, as conventional metrology approaches can be unable to accurately measure characteristics of features and/or films on a device as the size of those features/films decreases. For example, a conventional metrology system might be able to accurately provide the critical dimension of a 90 nm line, but might not be able to accurately provide the critical dimension of a 65 nm or 45 nm line. A conventional metrology system also might not be able to accurately characterize a film having a thickness of less than 10 nm. Using a liquid immersion approach as described above can provide for more accurate measurement of sample parameters using standard metrology techniques by increasing the resolution of the existing system.

As mentioned, the resolution of such a metrology system can be improved by utilizing an immersion liquid, having a relatively high index of refraction, between an optical element of the metrology system and the sample being evaluated. The resolution of the system can be determined using Rayleigh's criteria for resolution, given by:

$$d = \frac{1.22}{NA} * \left(\frac{\lambda}{n_i}\right)$$

where d is the resolution, λ is the wavelength of incident light, NA is the numerical aperture (given by NA=n*sin(θ)), and $n_i$ is the index of refraction of the medium through which the light is passing. Accordingly, the resolution of the system can be increased by increasing the index of refraction of the immersion liquid, decreasing the wavelength of the incident light, or increasing the acceptance angle of the objective lens. For example, the resolution can be increased by approximately 20% by immersing the sample in water ($n_i$=1.2) instead of leaving the sample in ambient air ($n_i$=1.0). Immersion liquids in addition to water can be used, which have increased indices of refraction. For example, immersion oils can be used which have indices of refraction on the order of 1.5-1.8. To further increase the resolution, the numerical aperture of the lens can be increased, such as up to a numerical aperture of about 1.0.

Placing an immersion liquid between the sample and the optics also can decrease the wavelength of light incident on the sample. The effective wavelength in the immersion liquid, $\lambda_i$, can be given by:

$$\lambda_i = \frac{1}{n_i}\lambda_0$$

where $n_i$ is the refractive index of the immersion liquid and $\lambda_0$ is the vacuum operating wavelength. The resolution of the system then can be improved by decreasing the wavelength of incident light.

It should be understood, however, that there can be a number of challenges to be overcome in using an immersion fluid with such a system. First and foremost can be the issue of sample contamination. Applying and completely removing an immersion liquid from the surface of a sample without leaving any contaminants or residuals on the surface can be difficult. Any contamination or impurities in the liquid can remain on the surface after removal. Further, the surface of the sample can be modified by certain fluids, which can diffuse into, or alter the surface of, the sample. Further, in order to ensure contact with all surfaces of the complex structures that can be included in such a sample, it can be desirable to select a liquid that is a good wetting agent. These agents can be more difficult to remove, however, and can result in a higher likelihood of residual material on the surface of the sample. The difficulty in removing these agents can further increase the cost and complexity of the system. Other problems with liquid immersion approaches exist, such as the presence of bubbles or voids in the liquid. Gases in the layers of the sample can release into the liquid, creating bubbles which can create undesirable scattering of the incident and/or reflected light in the liquid. Selection of an appropriate liquid can eliminate many of the problems associated with liquid immersion, such as those described above.

Fluid Chamber

Figure 3A:
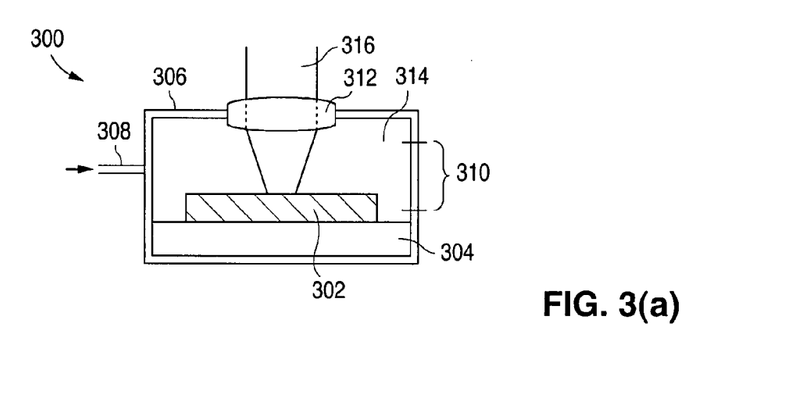
FIGS. 3(a) and (b) are diagrams of immersion fluid chambers that can be used with the system of FIG. 1.
Figure 3B:
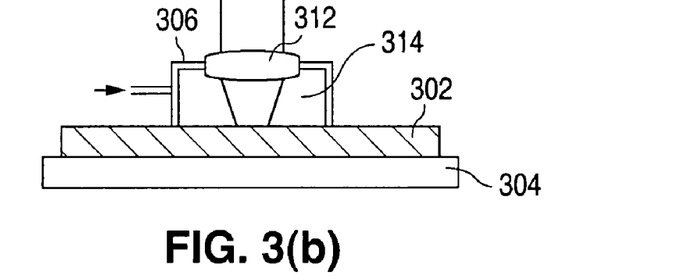

FIG. 3(a) shows a liquid immersion apparatus 300 that can be used in accordance with one embodiment of the present invention. In this embodiment, a sample 302 is held on a chuck 304, such as a vacuum chuck, of the immersion apparatus. The immersion apparatus can comprise a chamber 306 containing the chuck, or exposed to the chuck, which can hold the sample and an immersion fluid 314 therein. The chamber 306 can have a fluid inlet/outlet 308, allowing for fluid to be flowed into, and removed from, the chamber. The chamber also can have a door 310, or load lock, through which the sample 302 can be transferred to and from the chamber 306. The chamber can have a window 312 allowing a measurement beam to pass between the chamber and the metrology system, the window sealing the chamber such that the immersion fluid is contained within the chamber and air cannot enter into the immersion fluid. In one embodiment, the window can be a focusing lens or other optical element of the metrology system. In another embodiment as shown in FIG. 3(b), the fluid chamber 306 is sealably connected to only a portion of the sample surface, such that only a portion of the sample 302 will be exposed to the immersion fluid 314. The chamber 306 also can have an outlet (not shown) through which any gas in the chamber can be pumped out of the chamber in order to prevent voids or bubbles in the fluid. In the chamber, the sample 302 can be illuminated by light 316 from a light source (not shown) of the metrology system. The incident light can specularly reflect and/or scatter from the surface of the sample, and any patterns or features thereon. The light that is reflected from the sample can be directed to a detector (also not shown) for measurement, such as described with respect to FIG. 1.

Fluid Cassette

Figure 4:
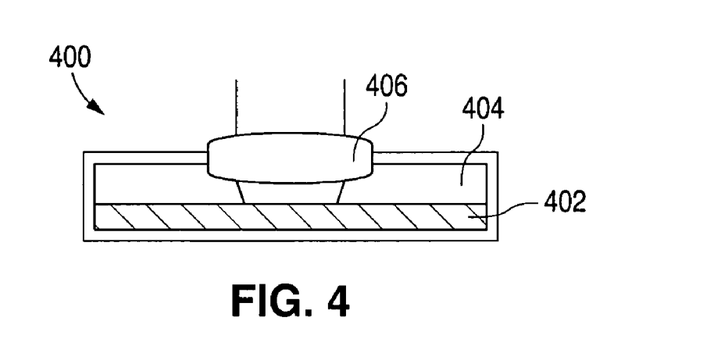
FIG. 4 is a diagram of an immersion fluid cassette that can be used with the system of FIG. 1.

In another embodiment, a sample 402 to be examined can be contained within a fluid cassette 400. The sample can be placed into the cassette, which can be filled with immersion fluid 404 and moved into the metrology system (not shown) for analysis. In order to ensure a smooth interface with the final metrology optic, the cassette can have an opening for sealably accepting the optic 406, or in some embodiments can have the optic built into the cassette such that the cassette can be filled with fluid, and have any gas removed, before being placed into the metrology system in order to minimize system downtime. In one example, each of a number of silicon wafers to be examined can be immersed in an immersion liquid in the cassette before being conveyed to the metrology system. In some embodiments, the window element 406 can simply comprise a parallel plane glass plate of an appropriate refractive index. Use of a flat plate can allow the cassette to be separated from the metrology optics, and can allow the cassette to be translated with respect to the metrology optics, such as through lateral movement of a mounting stage. A planar surface also can help to prevent gas voids or bubbles from being trapped at the surface of the plate during the filling of the cassette with immersion fluid.

Figure 5A:
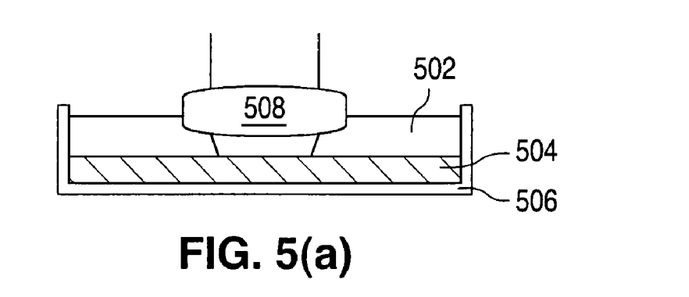
FIGS. 5(a) and (b) are diagrams of topless immersion fluid containers that can be used with the system of FIG. 1.

In another embodiment shown in FIG. 5(a), a fluid cassette can comprise an open container 506 into which the sample 504 can be lowered. The open cassette can be positioned in the metrology system and the optic 508 can be lowered into the immersion fluid 502 in the cassette. In order to minimize the chance of fluid spill, the cassette can be placed in the metrology system before the immersion fluid is flowed into the cassette. The fluid can be drained from the cassette before removal from the metrology system. A similar approach can be taken to the system chuck in another embodiment. Here, the chuck can include a topless compartment for containing the sample which can be filled with an immersion fluid. The chuck can be mounted to a translation stage such that the chuck can be moved away from the metrology optics in order to receive the sample, then can be translated into place and filled with the immersion fluid. The immersion fluid can be filled in such a way as to contact a final metrology optic and minimize the presence of gas voids or bubbles.

Figure 5B:
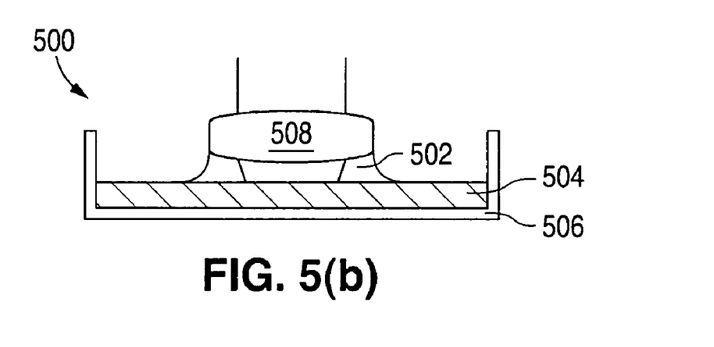

In another embodiment shown in FIG. 5(b), a drop or amount of immersion fluid 502 can be placed onto the surface of the sample 504, such as in a topless container 506, instead a full layer of immersion fluid as in FIG. 5(a), such that the liquid sufficiently contacts the metrology optic 508 and the sample 504, while minimizing the footprint of the immersion fluid on the sample. Alternatively, the liquid can be placed on the optic and brought into contact with the sample, or can be injected between the optic and the sample once the sample is in place.

Beam Profile Ellipsometry

Beam profile ellipsometry (BPE) is discussed in U.S. Pat. Nos. 5,042,951 and 5,181,080, as well as pending U.S. Patent Application Publication No. US 2003/0147086, each of which is commonly owned by the present assignee and is hereby incorporated herein by reference. Ellipsometry in general is a non-destructive optical metrology technique whereby properties of a sample, such as a thin film layer on a microdevice, are examined using a probe beam of polarized light. The properties examined can include, for example, profile information, layer thickness, chemical composition, and index of refraction. These properties can be obtained for the sample by analyzing the polarization state of light reflecting from, or transmitted through, the sample. The light can become elliptically polarized after interaction with the sample, with the shape and orientation of the polarization ellipse depending at least in part on the polarization and wavelength of the incident light, the angle of incidence, and the material properties of the surface. Ellipsometry is particularly useful for measuring samples such as thin films used in the fabrication of integrated circuits, including films of differing thickness. An ellipsometer usually can detect a change in film thickness on the order of tens of nanometers. An ellipsometer can measure the thickness and refractive index of thin films by measuring changes in the polarization state of light reflected from the thin films. By utilizing fluid immersion techniques described above, it can be possible to detect variations in film thickness on the order of a few nanometers or less.

In a basic BPE apparatus, a probe beam with a known polarization state is tightly focused with a high numerical aperture lens to a relatively small spot on a surface of a sample, at a direction substantially normal to the surface, and the polarization state of the reflected probe beam is analyzed. This tight focusing of the beam creates a spread of angles of incidence with respect to the sample surface of individual rays within the focused probe beam. The angle of incidence of one or more rays in the incident probe beam can be determined based on the radial position of the rays within the reflected probe beam. The means for analyzing the polarization state can include any of the components known in the prior art. Such an approach can provide enhanced spatial resolution and can allow for measurement over a wide spread of angles of incidence without adjusting the position of the optical components. Multiple angle of incidence measurements are then greatly simplified.

The analyzing means can include a detector which functions to determine the angle of incidence with respect to the sample surface of various rays within the incident probe beam. The angle of incidence of these rays can depend on the radial position of the rays within the reflected probe beam. More specifically, the rays in the center of the beam can represent the lowest angles of incidence relative to a normal, while the radially outer rays within the reflected probe beam correspond to progressively higher angles of incidence. By comparing the polarization state of the incoming beam with that of the beam after interaction with the sample, in relation to the angle of incidence, various parameters of the sample can be determined.

Using a liquid immersion approach with such a system allows a higher spread of angles of incidence to be generated without sacrificing the ability to tightly focus the beam. Moreover, the spread of incidence angles allows multiple angle of incidence measurements to be made without adjusting the position of the components. Furthermore, since the reflected probe beam comes back up from the sample through the same fluid and focusing optics, the system can be essentially self-aligning.

In a basic apparatus, a probe beam can be passed through a polarization section which in one embodiment includes a linear or circular polarizer and a birefringent quarter wave plate compensator. As is well known, certain lasers themselves are designed to emit light of a known polarization. Such a laser might be used to eliminate the need for a separate polarizer section. In either case, the combination of the laser and polarization section results in a known polarization state for the probe beam. After passing through the polarization section, the probe beam can be reflected downward, such as by a beam splitter, towards a sample. The sample can have any of a number of features and/or optically transmissive film layers thereon. The beam is directed substantially normal to the surface of the sample. The beam can be tightly focused on the surface of the sample with a high numerical aperture lens. After the probe beam reflects off the surface of the sample the beam is reflected back up through beam splitter into an analyzer module. The detector and processor can be arranged such that information about the angle of incidence, with respect to the sample surface, of rays within the incident probe beam are determined based on the radial position of the rays within the reflected probe beam. The ability to extract this information can be described with respect to FIG. 2(b), which illustrates individual rays within the incident focused probe beam. Where the beam is directed substantially normal to a surface of the sample, the incident focused beam can include a center ray incident upon the surface along normal line 210. The focused beam can also include outer rays 214 and 216, each having a maximum angle $\theta_r$ of incidence with respect to a surface of the sample. In three dimensions, these outer rays can correspond to a cone of light. The angle of incidence of each outer ray can be dependent upon the numerical aperture of lens in contact with the immersion fluid, as well as the refractive index of both the immersion fluid and the sample material. The focusing lens can be selected to have a high numerical aperture in order to maximize the spread of angles of incidence. In practice, a lens creating a spread of angles (from the center ray to the outermost ray) of at least 30° can be desired. A lens having a numerical aperture on the order of about 0.5 can provide such a spread of rays. In one embodiment, a lens having a 0.95 numerical aperture is used which gives a spread of greater than 70°. The detector and processor can function to measure the intensity of the reflected probe beam as a function of the angle of incidence of rays within the focused incident probe beam.

An example of such a BPE system 10 is shown in FIG. 1, which includes a quarter wave plate 34, polarizer 36, lens 38 and a detector 40. In operation, linearly polarized probe beam 24 is focused onto sample 4 by lens 32. An immersion fluid (not shown) can be placed between lens 32 and sample 4 such as by using one of the techniques described above. Light reflected from the sample surface can pass up through lens 32, through mirrors 42, 30 and 44, and can be directed into BPE 10 by mirror 46. The position of the rays within the reflected probe beam correspond to specific angles of incidence with respect to the surface of the sample surface. Quarter-wave plate 34 retards the phase of one of the polarization states of the beam by 90 degrees. Linear polarizer 36 causes the two polarization states of the beam to interfere with each other. For maximum signal, the axis of the polarizer 36 can be oriented at an angle of 45 degrees with respect to the fast and slow axis of the quarter-wave plate 34. In one embodiment, detector 40 is a detector capable of determining the location of a ray in the focused beam, such as an array detector, multi-element detector, or CCD detector, which can be provided to the processor in order to simultaneously associate each measurement with an angle of incidence. In another embodiment, detector 40 can be a quad-cell detector with four radially disposed quadrants (lying along two orthogonal axes) that each intercept one quarter of the probe beam and generate a separate output signal proportional to the power of the portion of the probe beam striking that quadrant. The output signal from each quadrant represents an integration of the intensity of various rays having different angles of incidence. The output signals from each quadrant can be sent to a processor 48, which can take the difference between the sums of the output signals of diametrically opposed quadrants, a value which varies linearly with film thickness for very thin films. As discussed in U.S. Pat. Nos. 5,042,951 and 5,181,080, monitoring the change in the polarization state of the beam allows ellipsometric information, such as $\Psi$ and $\Delta$, to be determined.

Beam Profile Reflectometry

Beam profile reflectometry (BPR) is discussed in U.S. Pat. No. 4,999,014, issued on Mar. 12, 1991, which is commonly owned by the present assignee and is incorporated herein by reference. FIG. 1 shows an exemplary BPR system 12, which includes a lens 50, beam splitter 52 and two linear detector arrays 54 and 56 to measure the reflectance of the sample. In operation, linearly polarized probe beam 24 is focused onto sample 4 by lens 32, with various rays within the beam striking the sample surface at a range of angles of incidence. Again, an immersion fluid can be placed between lens 32 and sample 4 using one of the techniques described elsewhere herein. Light reflected from the sample surface passes up through lens 32, through mirrors 42 and 30, and directed into BPR 12 by mirror 44. The position of the rays within the reflected probe beam correspond to specific angles of incidence with respect to the sample's surface. Use of an immersion fluid can increase the available angles of incidence, thereby increasing the amount of information that can be obtained from the sample for a given beam width and optics configuration. Lens 50 spatially spreads the beam two-dimensionally. Beam splitter 52 separates the S and P components of the beam, and detector arrays 54 and 56 are oriented orthogonal to each other to isolate information about S and P polarized light. The higher angles of incidence rays will fall closer to the opposed ends of the arrays. The output from each element in the diode arrays will correspond to different angles of incidence. Detector arrays 54, 56 measure the intensity across the reflected probe beam as a function of the angle of incidence with respect to the sample surface. The processor 48 receives the output of the detector arrays 54, 56, and derives the thickness and refractive index of the thin film layer 8 based on these angular dependent intensity measurements by utilizing various types of modeling algorithms. Optimization routines which use iterative processes such as least square fitting routines are typically employed. One example of this type of optimization routine is described in "Multiparameter Measurements of Thin Films Using Beam-Profile Reflectivity," Fanton, et. al., Journal of Applied Physics, Vol. 73, No. 11, p. 7035, 1993.

Combined Metrology Approaches

Processes such as BPR and BPE approaches discussed above can utilize at least two variable parameters when probing a sample, such as the wavelength and the angle of incidence. In BPR technology, for example, the probing wavelength can be fixed at the diode laser wavelength, and the polarized laser beam can be focused with a high numerical aperture objective lens to a spot size approaching the diffraction limit. In addition to providing a very small spot size, the objective lens produces a bundle of light with a light cone of, for example, 64 degrees, thereby simultaneously probing the sample at all angles between 0 and 64 degrees. Angular information thus obtained by the BPR system can be supplemented using another measurement module, such as a spectrometer capable of measuring the reflectivity at normal incidence as a function of wavelength. Spectroscopic BRE and BPR systems also can be used, which can measure reflectivity as a function of color and/or angle. In one such scatterometry module, for example, the processor can analyze reflectivity data according to a scattering model which permits evaluation of the geometry of a periodic structure. In one embodiment, a sample can be scanned with respect to the probe beam and output signals can be generated as a function of position of the probe beam spot.

Data obtained from simultaneous multiple angle of incidence measurements can be used as an input to analytical software designed to evaluate surface features via a specular scatterometry approach. The measurement data can be obtained from two or more metrology devices of the type described herein, as well as in the above identified PCT application. As more of these metrology devices are added, the ability to unambiguously distinguish features can increase. It therefore can be advantageous to utilize either or both of a simultaneous multiple angle of incidence spectrometer or ellipsometer along with one or more of spectroscopic reflectometry, spectroscopic ellipsometry or absolute ellipsometry tools, with the latter two being deployed in a manner that maximizes the information content of the measurement. For example, with a rotating compensator spectroscopic ellipsometer both the sign and magnitude of the ellipsometric phase are measured, while in more standard configurations, e.g., a rotating polarizer/rotating analyzer, only the magnitude or phase is measured.

Examples of analytical approaches for evaluating parameters and/or features using data from a broadband reflectometer are described in "In-situ Metrology for Deep Ultraviolet Lithography Process Control," Jakatdar et. al., SPIE Vol. 3332, pp. 262-270 1998; "Specular Spectroscopic Scatterometry in DUV Lithography, SPIE Vol. 3677, pp 159-168, from the SPIE Conference on Metrology, Inspection and Process Control for Microlithography XIII, Santa Clara, Calif., March 1999; and "Simultaneous Measurement of Six Layers in a Silicon on Insulator Film Stack Using Spectrophotometry and Beam Profile Reflectometry," Leng et al., J. Appl. Phys. 81 (8), April 1997.

As is known in the art, reflected output signals at multiple angles of incidence can be more rigorously analyzed to determine the specific geometry of the periodic structure. While there are a number of different approaches, most have certain traits in common. More specifically, the analytical approach will typically start with a theoretical "best guess" of the geometry of the measured structure. Using Fresnel equations covering both the reflection and scattering of light, calculations can be made to determine what the expected measured output signals would be at different angles of incidence for the theoretical geometry. These theoretical output signals can be compared to the actual measured output signals and the differences noted. Based on the differences, the processor can generate a new set of theoretical output signals corresponding to a different theoretical periodic structure. Another comparison can be made to determine if the theoretical signals are closer to the actual measured signals. These generation and comparison steps can be repeated until the differences between the theoretically generated data and the actually measured data are substantially minimized. Once the differences have been minimized, the theoretical periodic structure corresponding to the best fit theoretical data can be assumed to represent the actual periodic structure. Such a minimization procedure can be carried out with a conventional least squares fitting routine such as a Levenberg-Marquardt algorithm. It would also be possible to use a genetic algorithm, such as described in U.S. Pat. No. 5,953,446.

In addition to providing additional information about the sample, many of these additional metrology approaches also can benefit from the immersion fluid systems and methods discussed above. Examples of such approaches are shown in FIG. 1, which can have an immersion fluid positioned between sample 4 and lens 32 as described elsewhere herein, in order to improve the resolution and angular range of the metrology systems. Broadband Reflective Spectrometry is one such approach. An exemplary broadband reflective spectrometer (BRS) 14 simultaneously probes the sample 4 with multiple wavelengths of light. BRS 14 uses lens 32 and includes a broadband spectrometer 58 which can be of any type commonly known and used in the prior art. The spectrometer 58 shown in FIG. 1 includes a lens 60, aperture 62, dispersive element 64 and detector array 66. During operation, probe beam 26 from white light source 22 is focused onto sample 4 by lens 32. Light reflected from the surface of the sample passes up through lens 32, and is directed by mirror 42 (through mirror 84) to spectrometer 58. The lens 60 focuses the probe beam through aperture 62, which defines a spot in the field of view on the sample surface to analyze. Dispersive element 64, such as a diffraction grating, prism or holographic plate, angularly disperses the beam as a function of wavelength to individual detector elements contained in the detector array 66. The different detector elements measure the optical intensities of the different wavelengths of light contained in the probe beam, preferably simultaneously. Alternately, detector 66 can be a CCD camera, or a photomultiplier with suitably dispersive or otherwise wavelength selective optics. It should be noted that a monochrometer could be used to measure the different wavelengths serially (one wavelength at a time) using a single detector element. Further, dispersive element 64 can be configured to disperse the light as a function of wavelength in one direction, and as a function of the angle of incidence with respect to the sample surface in an orthogonal direction, so that simultaneous measurements as a function of both wavelength and angle of incidence are possible. These measurements thus can be improved using fluid immersion technologies discussed herein. Processor 48 processes the intensity information measured by the detector array 66.

Deep ultra violet reflective spectrometry (DUV) can simultaneously probe the sample with multiple wavelengths of ultra-violet light. DUV 16 uses the same spectrometer 58 to analyze probe beam 26 as BRS 14, except that DUV 16 uses the reflective lens 33 instead of focusing lens 32. To operate DUV 16, the turret containing lenses 32, 33 is rotated so that reflective lens 33 is aligned in probe beam 26. The reflective lens 33 is necessary because solid objective lenses cannot sufficiently focus the UV light onto the sample.

Broadband spectroscopic ellipsometry (BSE) is discussed in U.S. Pat. No. 5,877,859, which is commonly owned by the present assignee and is incorporated herein by reference. BSE (18) includes a polarizer 70, focusing mirror 72, collimating mirror 74, rotating compensator 76, and analyzer 80. In operation, mirror 82 directs at least part of probe beam 26 to polarizer 70, which creates a known polarization state for the probe beam, preferably a linear polarization. Mirror 72 focuses the beam onto the sample surface at an oblique angle, ideally on the order of 70 degrees to the normal of the sample surface. Based upon well known ellipsometric principles, the reflected beam will generally have a mixed linear and circular polarization state after interacting with the sample, based upon the composition and thickness of the sample's film 8 and substrate 6. The reflected beam is collimated by mirror 74, which directs the beam to the rotating compensator 76. Compensator 76 introduces a relative phase delay $\Delta$. (phase retardation) between a pair of mutually orthogonal polarized optical beam components. Compensator 8 is rotated at an angular velocity c about an axis substantially parallel to the propagation direction of the beam, preferably by an electric motor 78. Analyzer 80, preferably another linear polarizer, mixes the incident polarization states. By measuring the light transmitted by analyzer 80, the polarization state of the reflected probe beam can be determined. Mirror 84 directs the beam to spectrometer 58, which simultaneously measures the intensities of the different wavelengths of light in the reflected probe beam that pass through the compensator/analyzer combination. Processor 48 receives the output of the detector 66, and processes the intensity information measured by the detector 66 as a function of wavelength and as a function of the azimuth (rotational) angle of the compensator 76 about its axis of rotation, to solve the ellipsometric values $\Psi$ and $\Delta$ as described in U.S. Pat. No. 5,877,859.

A detector 86, or camera, can be positioned above mirror 46, and can be used to view reflected beams off of the sample 4 for alignment and focus purposes.

In one embodiment, a simple ellipsometer 2 can be used to calibrate the system devices by first determining the thickness of a film 8 on a sample being examined. After the thickness is determined, the same sample 4 can be probed by any or all of the other optical measurement devices shown in the example of FIG. 1, including devices for BPE 10, BPR 12, BRS 14, DUV 16, and BSE 18, which measure various optical parameters of the sample 4. A processor 48 then can calibrate the processing variables used to analyze the results from these optical measurement devices such that the devices produce accurate results. For each of these measurement devices, there can be system variables that affect the measured data and need to be accounted for before an accurate measurement of other samples can be made. In the case of BPE 10, the most significant variable system parameter can be the phase shift that occurs due to the optical elements along the BPE optical path. For BSE 18, multiple phase offsets can be derived for multiple wavelengths in the measured spectrum. For the remaining measurement devices, BPR 12, BRS 14 and DUV 16, the measured reflectances can be affected by environmental changes to the optical elements in the beam paths. Therefore, the measurements made by the BPR/BRS/DUV devices for any other sample can be scaled by processor 48 using a normalizing factor obtained in the calibration.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

What is claimed is:

1. An apparatus for measuring a parameter of a sample, comprising:
    a radiation source for generating a probe beam;
    an optical element having a numerical aperture of at least 0.5 for focusing said probe beam onto the surface of the sample such that various rays within the focused probe beam create a spread of angles of incidence with respect to said sample;
    an immersion fluid between the optical element and the sample for increasing the spread of angles of incidence;
    a detector receiving the probe beam after the probe beam has been reflected from the sample, said detector measuring the intensity of various rays as a function of position within the reflected probe beam, with the position of the rays within said reflected probe beam corresponding to specific angles of incidence with respect to said sample; and
    a processor for determining a parameter of the sample based on the intensity measurements, said parameter being selected from the group consisting of material composition, thickness, index of refraction, absorption, stress, feature width, critical dimension, profile dimension, and surface roughness.

2. An apparatus as recited in claim 1, wherein the probe beam is directed substantially normal to the surface of the sample.

3. An apparatus as recited in claim 2, wherein said detector is a two-dimensional array.

4. An apparatus as recited in claim 1, further including a retarding element capable of retarding the phase of one polarization state in the probe beam with respect to the phase of the other polarization state in the probe beam and a polarizing element capable of creating interference between the two polarization states in the probe beam after the probe beam has been reflected from the surface of the sample.

5. An apparatus as recited in claim 4, wherein the processor determines the change in polarization state of the probe beam.

6. An apparatus as recited in claim 1, wherein said radiation source is a laser.

7. An apparatus as recited in claim 1, wherein the numerical aperture of the focusing element is on the order of 0.95.

8. An apparatus for measuring a parameter of a sample, comprising:
    a radiation source for generating a probe beam;
    an optical element focusing said probe beam onto the surface of the sample such that various rays within the focused probe beam create a spread of angles of incidence with respect to said sample;
    an immersion fluid between the optical element and the sample for increasing the spread of angles of incidence;
    a detector receiving the probe beam after the probe beam has been reflected from the sample, said detector measuring the intensity of the probe beam; and
    a processor for determining a parameter of the sample based on the intensity measurement, said parameter being selected from the group consisting of material composition, thickness, index of refraction, absorption, stress, feature width, critical dimension, profile dimension, and surface roughness.

9. An apparatus as recited in claim 8, wherein said radiation source is a broadband source and the probe beam is measured as a function of wavelength.

10. An apparatus as recited in claim 9, wherein said detector is an array detector and further including a grating for dispersing the reflected light as a function of wavelength.

11. An apparatus as recited in claim 9, wherein the probe beam is directed substantially normal to the surface of the sample.

12. An apparatus as recited in claim 8, wherein said detector is an array detector for measuring the intensity of various rays as a function of position within the reflected probe beam, with the position of the rays within said reflected probe beam corresponding to specific angles of incidence with respect to said sample.

13. An apparatus as recited in claim 8, wherein the processor determines the change in polarization state of the probe beam.

14. An apparatus as recited in claim 8, further including a retarding element capable of retarding the phase of one polarization state in the probe beam with respect to the phase of the other polarization state in the probe beam and a polarizing element capable of creating interference between the two polarization states in the probe beam after the probe beam has been reflected from the surface of the sample.

15. An apparatus as recited in claim 14, wherein said detector measures the intensity of the reflected probe beam along two orthogonal axes after the probe beam has passed through the retarding and polarizing elements, the detector generating an output that integrates the intensity of various rays having different angles of incidence, the output having two components corresponding to said two orthogonal axes.

16. An apparatus as recited in claim 15, wherein said detector is a quad cell.

17. An apparatus for measuring a parameter of a sample, comprising:
    a laser for generating a probe beam;
    an lens assembly having a numerical aperture of at least 0.5 for focusing said probe beam substantially normal onto the surface of the sample such that various rays within the focused probe beam create a spread of angles of incidence with respect to said sample;
    an immersion fluid between the optical element and the sample for increasing the spread of angles of incidence;
    an array detector receiving the probe beam after the probe beam has been reflected from the sample, said detector measuring the intensity of various rays as a function of position within the reflected probe beam, with the position of the rays within said reflected probe beam corresponding to specific angles of incidence with respect to said sample; and
    a processor for determining a parameter of the sample based on the intensity measurements.

18. An apparatus as recited in claim 17, wherein the numerical aperture of the focusing element is on the order of 0.95.

* * * * *